United States Patent
Gagnon et al.

(10) Patent No.: US 8,437,836 B2
(45) Date of Patent: May 7, 2013

(54) REVERSE DATA RECONSTRUCTION FOR OPTIMAL TIME SAMPLING OF COUNTS IN PHYSIOLOGICAL LIST-MODE NUCLEAR IMAGING

(75) Inventors: Daniel Gagnon, Twinsburg, OH (US); Sameer Tipnis, Mayfield Village, OH (US); Raymond Muzic, Mentor, OH (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 77 days.

(21) Appl. No.: 12/995,685

(22) PCT Filed: May 29, 2009

(86) PCT No.: PCT/IB2009/052290
§ 371 (c)(1),
(2), (4) Date: Dec. 2, 2010

(87) PCT Pub. No.: WO2009/150565
PCT Pub. Date: Dec. 17, 2009

(65) Prior Publication Data
US 2011/0105887 A1    May 5, 2011

Related U.S. Application Data

(60) Provisional application No. 61/061,289, filed on Jun. 13, 2008.

(51) Int. Cl.
*A61B 6/00* (2006.01)
(52) U.S. Cl.
USPC ........... 600/436; 600/407; 600/410; 382/128; 382/131; 382/132

(58) Field of Classification Search .......... 600/407–469, 600/473–480; 382/128–132
See application file for complete search history.

(56) References Cited

U.S. PATENT DOCUMENTS

| | | | |
|---|---|---|---|
| 4,569,590 A | * | 2/1986 | Karny et al. .................. 356/128 |
| 5,841,140 A | * | 11/1998 | McCroskey et al. ..... 250/363.03 |

(Continued)

FOREIGN PATENT DOCUMENTS

| | | |
|---|---|---|
| WO | 2007074467 A2 | 7/2007 |
| WO | 2007149453 A2 | 12/2007 |

OTHER PUBLICATIONS

Anonymous; Automation of gated PET-CT workflow; 2006; IP.Com Journal; IP.Com Inc., West Henrietta, NY.

(Continued)

*Primary Examiner* — Sanjay Cattungal

(57) ABSTRACT

A diagnostic imaging device includes detector elements (16) for detecting γ-rays indicative of nuclear decay events. Pairs of concurrently detected γ-rays define lines of response (LORs) which are collected, time stamped, and compiled in list-mode. In tissue perfusion studies, it is beneficial to use the data that concurrently maximizes contrast and signal-to-noise ratio in the reconstructed images. Using the list-mode data, events in an adjustable temporal window (33) are reconstructed and the reconstructed images are analyzed to determine a figure of merit based on contrast and signal-to-noise properties of the image. By iteratively adjusting the temporal window, extending its start point (36) backwards in time, and repeating the reconstructing, analyzing, and adjusting steps, an image with an optimal figure of merit is obtained.

18 Claims, 3 Drawing Sheets

U.S. PATENT DOCUMENTS

| | | | | |
|---|---|---|---|---|
| 6,072,177 | A * | 6/2000 | McCroskey et al. | 250/252.1 |
| 6,255,655 | B1 * | 7/2001 | McCroskey et al. | 250/363.03 |
| 7,132,664 | B1 * | 11/2006 | Crosetto | 250/367 |
| 7,411,199 | B2 * | 8/2008 | Vernon | 250/370.08 |
| 7,705,316 | B2 * | 4/2010 | Rousso et al. | 250/370.09 |
| 7,732,774 | B2 * | 6/2010 | Majewski | 250/363.04 |
| 7,858,944 | B2 * | 12/2010 | Majewski et al. | 250/363.03 |
| 7,968,851 | B2 * | 6/2011 | Rousso et al. | 250/370.09 |
| 8,000,773 | B2 * | 8/2011 | Rousso et al. | 600/436 |
| 8,094,894 | B2 * | 1/2012 | Nagler et al. | 382/128 |
| 8,111,886 | B2 * | 2/2012 | Rousso et al. | 382/128 |
| 8,116,844 | B2 * | 2/2012 | Schmidt | 600/420 |
| 2003/0016852 | A1 * | 1/2003 | Kaufman et al. | 382/131 |
| 2004/0210132 | A1 | 10/2004 | Manjeshwar | |
| 2005/0123183 | A1 | 6/2005 | Schleyer et al. | |
| 2006/0231777 | A1 * | 10/2006 | Vernon | 250/526 |
| 2008/0042067 | A1 * | 2/2008 | Rousso et al. | 250/363.04 |
| 2008/0073538 | A1 * | 3/2008 | Vija et al. | 250/363.04 |
| 2008/0087833 | A1 * | 4/2008 | McCroskey et al. | 250/370.08 |
| 2008/0128626 | A1 * | 6/2008 | Rousso et al. | 250/362 |
| 2008/0230702 | A1 * | 9/2008 | Rousso et al. | 250/363.02 |
| 2008/0230705 | A1 * | 9/2008 | Rousso et al. | 250/363.04 |
| 2009/0078875 | A1 * | 3/2009 | Rousso et al. | 250/363.04 |
| 2009/0304582 | A1 * | 12/2009 | Rousso et al. | 424/1.61 |
| 2010/0021378 | A1 * | 1/2010 | Rousso et al. | 424/1.11 |
| 2011/0064295 | A1 * | 3/2011 | Gagnon et al. | 382/131 |

OTHER PUBLICATIONS

Groves, A.M., et al.; Cardiac (82) rubidium PET/CT: Initial european experience; 2007; European Journal of Nuclear Medicine and Molecular Imaging; 34(12)abstract.

Meyer, C., et al.; Assessment of input function distortions on kinetic model parameters in simulated dynamic Rb-82 PET perfusion studies; 2007; Nuclear Instruments & Methods in Physics Research-Section A-Accelerators Spectrometers Detectors and Associated Equipment; 571(1-2)abstract.

* cited by examiner

REVERSE DATA RECONSTRUCTION FOR OPTIMAL TIME SAMPLING OF COUNTS IN PHYSIOLOGICAL LIST-MODE NUCLEAR IMAGING

CROSS REFERENCE TO RELATED APPLICATIONS

This application claims the benefit of U.S. provisional application Ser. No. 61/061,289 filed Jun. 13, 2008, which is incorporated herein by reference.

The present application relates to the diagnostic imaging arts. It finds particular application in a nuclear medicine scanner that utilizes list-mode data acquisition, and will be described with particular reference thereto. It is to be understood, however, that it also finds application in other tracer perfusion studies, and is not necessarily limited to the aforementioned application.

The capture of physiological processes with nuclear dynamic imaging is a complex process requiring optimization of the sampling for the particular imaging system and an understanding of the phenomena involved in the tracer uptake. For example, cardiac perfusion studies using a rubidium-82 ($^{82}$Rb) injection and PET imaging combines the challenge of dynamically imaging a high flux, short half life isotope (about 90 seconds) and an uptake process that can extract $^{82}$Rb from the blood stream in as short as 30 seconds or as long as 200 seconds, depending on the subject, in a typical 360 second scan. Initially, there is a large amount of tracer in the blood, but little taken up by the area of interest. This generates a large amount of data, but with poor contrast. As time progresses in the scan, more of the tracer reaches and is taken up by the area of interest and is cleared from the blood, but concurrently, signal strength wanes as time goes on due to the natural decay of the tracer. This results in good contrast, but a low amount of data. There is difficulty in finding the optimal time for imaging that harmonizes signal strength and contrast.

The quality of the reconstructed images is dependent on the choice of the reconstruction interval. Choosing a longer reconstruction time interval, such as 90-360 seconds, can maximize the signal strength, that is, it can maximize the counts received. This comes at the expense of contrast. For example, in imaging the heart, the above selected time range might result in low contrast since blood in the ventricles, not yet absorbed by the tissues of the heart, may still be active. Because the early data has the highest count rate, it tends to dominate the lower count rate later data. On the other hand, if a window of 300-360 seconds is selected, the image will most likely have good contrast, as most of the tracer has been absorbed by the tissue of interest. There may be significant noise, however, as most of the tracer will have decayed by that time, leading to a low event count rate.

The present application provides a new and improved event processing method that is able to leverage list-mode data to efficiently optimize the image quality.

In accordance with one aspect, a diagnostic imaging apparatus is provided. A detector array including individual detectors senses photons emitted by radioactivity decay within the patient. A triggering processor assigns a time stamp to received potential events. An event verification processor applies verification criteria to received potential events. A reconstruction processor reconstructs valid events into an image representation of the imaging region. A figure of merit analyzer analyzes a reconstructed image to determine a figure of merit.

In accordance with another aspect, a method of diagnostic imaging is provided. A set of data points indicative of nuclear decay events is collected and the data points are sorted according to a time that the data points were detected. A reference point in time is selected. An image representation is reconstructed from data points occurring before the reference point. A figure of merit associated with the image representation is determined. A time interval is selected and applied backwards from the reference point creating a new reference point.

In accordance with another aspect, a method of diagnostic imaging is provided. Photons emitted in radioactive decay are detected. A time stamp is assigned to received potential events. Verification criteria are applied to received events. Valid events are reconstructed into an image representation of the imaging region. A reconstructed image is analyzed to determine a figure of merit.

One advantage lies in the ability to select an optimal combination of signal strength and image contrast in a nuclear tracer perfusion study.

Another advantage lies in the ability to iteratively add data to or remove data from a reconstructed image until a maximum image quality is achieved.

Another advantage is that it is easily retrofitted into present scanners provided that the scanners have compatible data generation and data format (e.g. list mode).

Still further advantages of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

Figure 1:
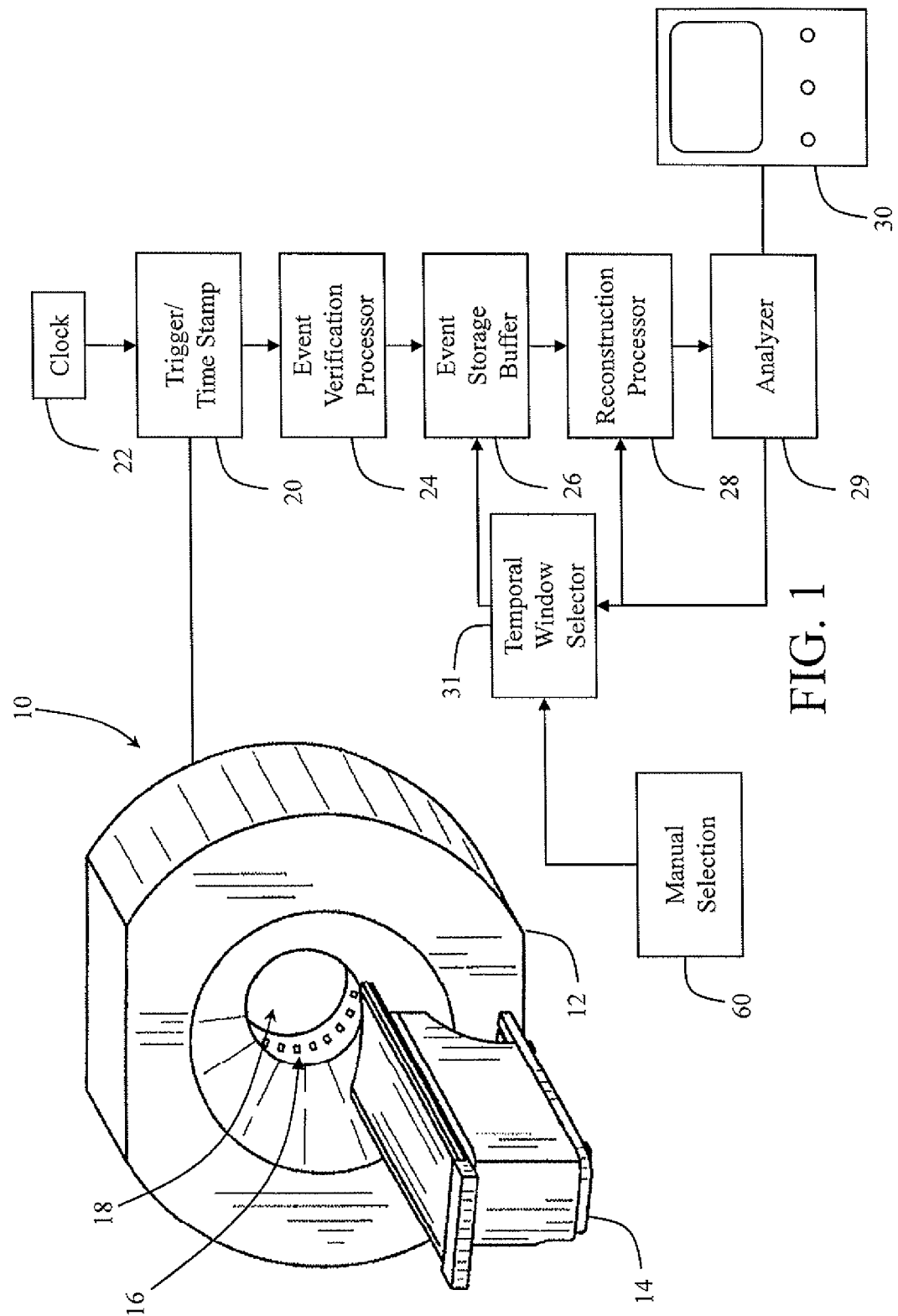
FIG. 1 is a diagrammatic illustration of a nuclear imaging device in accordance with the present application.

With reference to FIG. 1, a diagnostic imaging device 10 includes a housing 12 and a subject support 14. Enclosed within the housing 12 is a detector array. The detector array includes a plurality of individual detector elements 16. While one particular embodiment is described with reference to a positron emission tomography (PET) scanner, it is to be understood that the present application is also useful in other medical applications, such as single photon emission computed tomography (SPECT) as well as x-ray astrophysics, gamma ray telescopes, radiography, security, and industrial applications. Generally, the present application finds use in imaging x-rays, gamma rays, or charged particles with high energy and spatial resolution. The array is arranged so that detector elements 16 are disposed adjacent to an imaging region 18. The detector array can be a ring of detectors 16, multiple rings, one or more discrete flat or arced panels, or the like. In positron emission tomography (PET), pairs of gamma rays are produced by a positron annihilation event in the imaging region and travel in approximately opposite directions. Such an event may be produced from the nuclear decay of $^{82}$Rb. These gamma rays are detected as pairs, with a slight time difference (on the order of nanoseconds or fractions thereof) between detections if one gamma ray travels farther to reach a detector than the other. Accordingly, in PET scanners, the detector arrays typically encircle the imaging region.

Before the PET scan commences, a subject is injected with a radiopharmaceutical. In one common exam, the radiopharmaceutical contains a radioactive element, such as $^{82}$Rb, coupled to a tag molecule. The tag molecule is associated with the region to be imaged, and tends to gather there through body processes. For example, rapidly multiplying cancer cells tend to expend abnormally high amounts of energy duplicating themselves. The radiopharmaceutical can be linked to a molecule, such as glucose, or an analog thereof, that a cell typically metabolizes to create energy, which gathers in such regions and appear as "hot spots" in the image. Such a tag is also useful in cardiac perfusion imaging, since the heart expends relatively large amounts of energy. Other techniques monitor tagged molecules flowing in the circulatory system. In such a technique, it is beneficial to tag a molecule that is not quickly absorbed by tissues of the body.

When a gamma ray strikes the detector array, a time signal is generated. A triggering processor 20 monitors each detector 16 for an energy spike, e.g., integrated area under the pulse, characteristic of the energy of the gamma rays generated by the radiopharmaceutical. The triggering processor 20 checks a clock 22 and stamps each detected gamma ray with a time of leading edge receipt stamp. The time stamp, energy estimate and position estimation is first used by an event verification processor 24 to determine if the event data is valid, e.g., if the pair of events are coincident, have the proper energy, and the like. Accepted pairs define lines of response (LORs). Because gamma rays travel at the speed of light, if detected gamma rays arrive more than several nanoseconds apart, they probably were not generated by the same annihilation event and are usually discarded. Timing is especially important in time of flight PET (TOF-PET), as the minute difference in substantially simultaneous coincident events is used to further localize the annihilation event along the LOR. As the temporal resolution of events becomes more precise, so too does the accuracy with which an event can be localized along its LOR.

LORs are stored in an event storage buffer 26. In one embodiment, the LORs are stored in a list-mode format. That is, the events are stored in temporal order with time indicators periodically inserted. Alternatively, the events can be individually time stamped. A reconstruction processor 28 reconstructs all or a portion of the LORs into an image representation of the subject using filtered backprojection or other appropriate reconstruction algorithms. An analyzer 29 analyzes a reconstructed image to determine a figure of merit or other indicator of image quality. The analyzer 29 indexes a temporal window selector 31 to adjust the temporal window that defines a portion of the LORs that are reconstructed until the image quality is optimized or reaches a preselected level. This process is described in more detail hereinbelow. The reconstruction can then be displayed for a user on a display device 30, printed, saved for later use, and the like.

In one embodiment, event data is collected in a "list-mode" format. Recording the relevant properties of each detected event in a list has become a common practice in emission tomography applications and has become known as list-mode data acquisition and storage. The list-mode reconstruction approach differs in several ways from binned or histogrammed-mode methods. List-mode data acquisitions provide extremely high temporal resolution with full spatial resolution and allows frame durations to be determined after acquisition. Acquiring the data in list-mode format, the interaction location can be stored to a high degree of accuracy with greater efficiency than achievable with frame mode acquisition. Gantry angles do not have to be binned into predefined frames, but can be recorded as the actual angle, thereby removing the impact of angular blurring with continuous acquisition. The actual energy of the interaction can be recorded instead of attributing the event's energy to one of a limited number of pre-defined windows. When increasing the dimensionality in this way, the data is stored in a list where it can be arranged and sorted by several different parameters, e.g. time of receipt, instead of a bin. List-mode can also store gating signals without temporally framing of the data before this information is completely available. The result is a significant increase in the fidelity of recording the projection data with list-mode acquisition, without a tremendous increase in storage space. Another advantage is the ability to identify events by the time of their occurrence, and beneficially to the present application, being able to select a window of time in which the most optimal combination of contrast and signal strength is observed.

Figure 2:
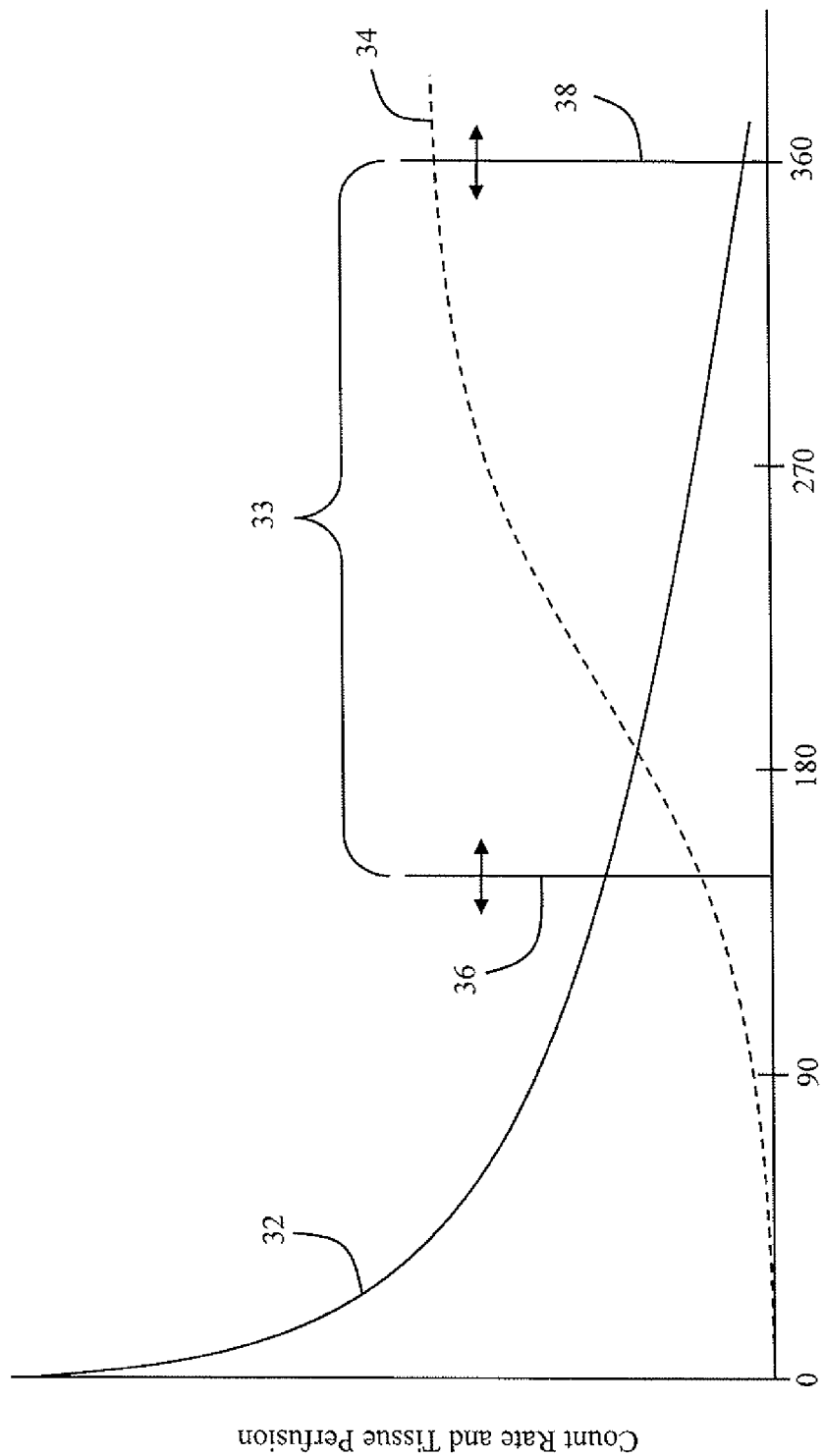
FIG. 2 is a graph showing count rate and tissue perfusion as functions of time.

With reference to FIG. 2, the most optimal quality of a reconstructed image is achieved by a judicious choice of the reconstruction interval or window 33 within the time span of the data acquisition. During the data acquisition, e.g., 360 seconds, the count rate 32 is highest at the beginning, decreasing toward the end. Conversely, the contrast 34 is lowest at the beginning of the scan. The LORs collected in the selectable temporal window 33 are reconstructed. The start 36 of the window and/or the end 38 are selectively adjusted to optimize the balance between contrast and count rate. Of course, multiple windows, including overlapping windows, can be defined and an image reconstructed for each.

Figure 3:
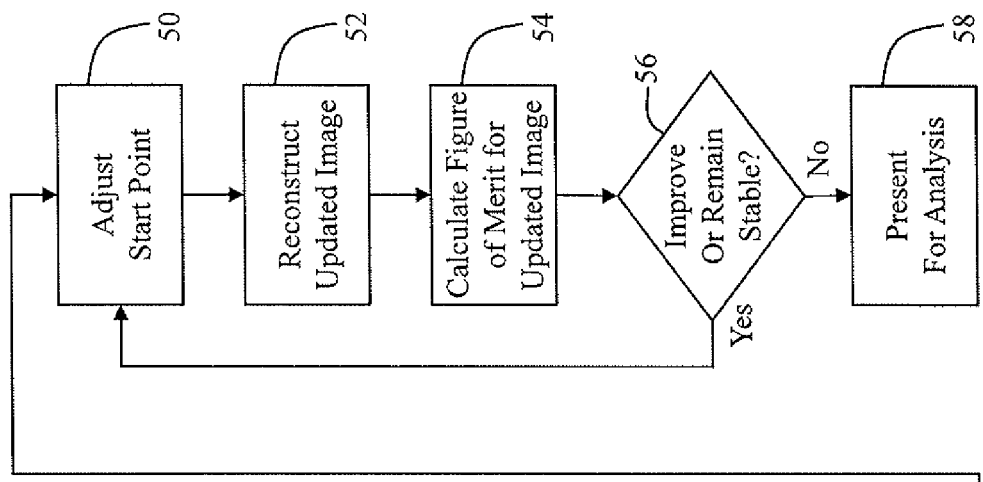
FIG. 3 is a flow diagram of an iterative determination of the most valuable data to be used in reconstruction, in accordance with the present application.
Figure 3:
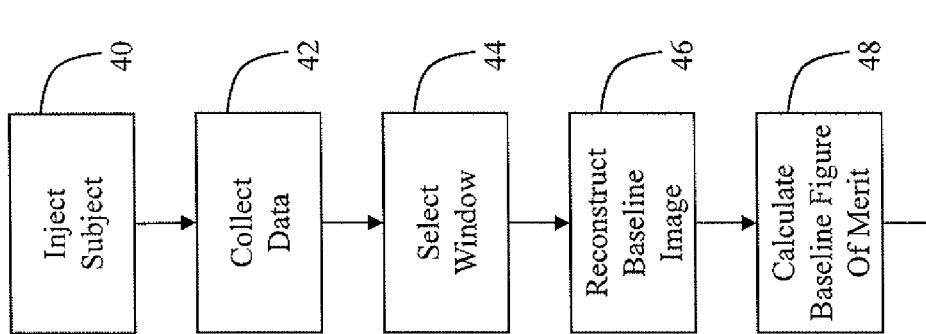

With reference now to FIG. 3, a flowchart describing image optimization is provided. First, the subject is injected with the radiopharmaceutical 40. The data is collected 42 and time stamped during the scan. The time of the data collection can vary depending on the radioactive material used to produce the annihilation events. In the case of $^{82}$Rb, the scan typically lasts about six minutes (360 seconds). In this time period, physically only one-sixteenth of the original amount of $^{82}$Rb will remain, and it is expected that the count rate will have become too low to be diagnostically useful.

After the data has been collected, the window as defined by the initial or start point and the terminal or end point are selected 44. In one embodiment, the terminal or end point 38 is selected to be a few seconds from the end of the scan. As mentioned previously, this data is most likely to provide the highest contrast image reconstruction, as the tracer has been given ample time to profuse to the tissue of interest. Using data from the very end of the scan is a universally applicable approach, and is useful especially when little is known of the physiology of the subject (human or animal) with respect to profusion.

If more is known, more significant points can be selected. For instance, with $^{82}$Rb in cardiac imaging, 200 seconds should be enough time for healthy human subjects. More generally, if there is a time at which it is known that the physiology of the subject should be in a steady state with respect to the variable to be measured, the window can be selected to be on or about that time. Further, there may be a parameter that can differentiate an intermediate state from the final steady state. Again in an example, in $^{82}$Rb cardiac imaging, the ratio of the myocardium activity compared to the blood stream (e.g., cavity of the ventricle) should be an indicator of the process.

Next, a baseline image is reconstructed 46. In one embodiment, the baseline image is reconstructed using data from the start point until the end of the scan. This baseline image includes high-contrast data counts, but if the start point is set late, the volume of the counts is low, leading to a low signal-to-noise ratio. The baseline image is evaluated to determine a figure of merit 48. In one embodiment, the figure of merit is the contrast-to-noise ratio. Other figures of merit are certainly contemplated, such as raw event count per unit time, and others.

Given the specified figure of merit for the baseline image, the start point is adjusted 50, e.g., moved earlier to increase the number of counts in an effort to improve the specified figure of merit. LORs in the increased region of the window are added to the LORs that were used to reconstruct the baseline image, and an updated image is reconstructed 52. Once the updated image has been reconstructed, the figure of merit is re-calculated for the new, updated image 54. If the figure of merit improves or remains stable within some selected statistical confines of the test, shown as decision block 56 in FIG. 3, the start event may be further adjusted (e.g., moving a small time period backwards, using a binary search, or a selected optimization algorithm) and the process repeated. The image that achieves the best figure of merit is used for further analysis 58, display, interpretation, or retained for future use. The start and end times also be displayed to the user, as uptake times can have significant diagnostic value.

In the same fashion, the end point for the window may optionally be adjusted. Data at the end of the scan may become less valuable as fewer counts occur. The end point of the window may be stepped backwards in time, and the updated image 52 is reconstructed. The new figure of merit is again re-calculated 54 until it ceases to improve. Optimization of the end point can occur either before or after optimization of the start point. During the described window selection process, the window 33 can be displayed to a user so the user can use it for aid in analyses, quantification, or diagnoses. The optimized window 33 can also be used by the system as a parameter in computer assisted diagnosis, as the uptake times and efficiencies can be indicative of body processes and function.

In one embodiment, the above-described process is automated, performed by the analyzer 29. It is contemplated that varying levels of user input can be accepted to aid in the decision. For example, the beginning and/or end time can be set by a user with a user input 60. For example, the user could drag the start and end time indicators in a display analogous to FIG. 2. The user may be prompted to decide whether the figure of merit has improved in a particular image relative to its predecessor. When the analyzer 29 comes to a decision on which image is the best, it may present it and several prior and subsequent images to the user for review. In this embodiment, the process is still largely automated, but with user analysis to supplement. The levels of user input and feedback desired would be selectable, and able to be toggled on or off at will.

In an alternate embodiment, the data can be compiled in a non-list-mode format. This embodiment present an additional problem of sorting events by time after they have already been binned, requiring extra processing power and time.

Some radiopharmaceuticals are absorbed by different tissue types within the body at different rates. Thus, the optimum image for different parts of the body might have different reference points. Accordingly, a plurality of optimized images may be displayed. As another alternative, a series of cine images could be displayed that show the uptake and washout over time. The time window corresponding to each of the cine images can be optimized in the same way.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A diagnostic imaging apparatus comprising:
   a detector array for receiving events from an imaging region;
   a triggering processor for assigning a time stamp to the received events;
   a reconstruction processor that reconstructs an adjustable portion of the events that fall in a temporal window into an image representation;
   an analyzer that analyzes the reconstructed image representation to determine a parameter indicative of image quality and adjusts the adjustable portion of the verified events by adjusting the temporal window in accordance with the determined parameter, the reconstruction processor reconstructing the adjusted portion of the verified events in the adjusted temporal window into a subsequent image representation;
   wherein the reconstruction processor and the analyzer iteratively repeat the analyzing, adjusting the temporal window, and reconstructing until the determined parameter meets a preselected criteria.

2. The diagnostic imaging apparatus as set forth in claim 1, wherein the determined parameter is a figure of merit based on a selected parameter of the image representation.

3. The diagnostic imaging apparatus as set forth in claim 1, further including:
   an event storage buffer that stores verified events in a list by time of receipt of the event.

4. The diagnostic imaging apparatus as set forth in claim 1, further including:
   a display configured for displaying at least one of the reconstructed image representations and an indication of the temporal window in which the reconstructed events fall to a user.

5. A method of diagnostic imaging comprising:
   collecting a set of data points indicative of received nuclear decay events;
   time stamping the received events;
   reconstructing an image representation from an adjustable portion of the collected data points that fall in a temporal window;
   analyzing the image representation to determine a value of a parameter indicative of image representation quality;
   adjusting the adjustable portion of the collected data points which are used in reconstructing a subsequent image representation by adjusting the temporal window in accordance with the determined parameters.

6. The method as set forth in claim 5, wherein the parameter determining step includes:
   determining a figure of merit for the image representation.

7. The method as set forth in claim 6, further including:
   comparing the figure of merit for the subsequent image representation to the figure of merit for the previous image representation, and if the figure of merit for the subsequent image representation is greater than or equal to the figure of merit for the previous image representation, repeating further adjusting the portion of the collected data points that are used to reconstruct a next image representation.

8. The method as set forth in claim 5, wherein the portion of the collected data points used in reconstructing the subsequent image representation is adjusted based on the determined value and is different from the portion of the collected data points used to reconstruct the previous image representation.

9. The method as set forth in claim 8, wherein the parameter value is indicative of a contrast of the image representation.

10. A nuclear imaging system including a processor programmed to control the nuclear imaging system to perform the method of claim 5.

11. The method as set forth in claim 5, further including:
    storing the data points by time of detection in a memory, the portion of the data points reconstructed into the image representation being in an adjustable detection time window.

12. The method as set forth in claim 11, further including:
    analyzing the subsequent image representation to determine a value of the parameter indicative of a quality of the subsequent image representation;
    in response to the determined values indicating that the subsequent image is better than the previous image, adjusting the detection time window and generating another image representation.

13. The method as set forth in claim 11, further including:
    displaying in indication of the detection time window and at least a one of the image representations reconstructed from the portion of data points in the indicated detection time window to a user.

14. The method as set forth in claim 11, further including:
    analyzing the window to aid in one of a diagnosis, quantification, and a measure of a bodily process.

15. A method of diagnostic imaging comprising:
    collecting a set of data points indicative of received nuclear decay events;
    time stamping the received events;
    storing the data points by time of detection in a memory, the portion of the data points reconstructed into the image representation being in an adjustable temporal time window, the temporal window having a start point and an end point;
    reconstructing an image representation from an adjustable portion of the collected data points;
    analyzing the image representation to determine a value of a parameter indicative of image representation quality;
    adjusting the adjustable portion of the collected data points which are used in reconstructing a subsequent image representation;
    analyzing the subsequent image representation to determine a quality of the subsequent image representation; and
    in response to the subsequent image being of better quality than the previous image representation, adjusting the temporal window by moving the start point toward a beginning of the scan and generating another image representation.

16. A method of diagnostic imaging comprising:
    collecting a set of data points indicative of received nuclear decay events;
    time stamping the received events;
    reconstructing an image representation from a portion of the collected data points falling in a temporal window;
    analyzing the image representation to determine a value of a parameter indicative of image representation quality;
    adjusting the temporal window and reconstructing the collected data points which fall in the adjusted temporal window into a subsequent image representation;
    iteratively repeating the steps of adjusting, reconstructing, and analyzing until a subsequent image representation with value of the parameter is one of optimized or exceeds a selected threshold is reconstructed.

17. A non-transitory computer readable medium carrying software to control a processor to perform the method of claim 16.

18. A diagnostic imaging apparatus comprising:
    a detector array configured to receive radiation events from an imaging region;
    a processor programmed to perform the method of claim 16.

* * * * *